United States Patent
Dorsel (10) Patent No.: US 7,504,072 B2
(45) Date of Patent: Mar. 17, 2009

(54) BIOPOLYMERIC ARRAY SCANNING DEVICES THAT FOCUS ON THE FAR SIDE OF AN ARRAY AND METHODS FOR USING THE SAME

(75) Inventor: Andreas N. Dorsel, Menlo Park, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 721 days.

(21) Appl. No.: 10/262,213

(22) Filed: Sep. 30, 2002

(65) Prior Publication Data

US 2004/0063106 A1    Apr. 1, 2004

(51) Int. Cl.
| | |
|---|---|
| *C12Q 1/00* | (2006.01) |
| *C12Q 1/68* | (2006.01) |
| *C12M 1/36* | (2006.01) |
| *C12M 3/00* | (2006.01) |
| *C12M 1/34* | (2006.01) |
| *G01N 21/00* | (2006.01) |
| *G01N 21/03* | (2006.01) |
| *G01N 21/76* | (2006.01) |
| *G01N 33/566* | (2006.01) |
| *G01N 15/06* | (2006.01) |
| *G01N 21/64* | (2006.01) |
| *B01L 9/00* | (2006.01) |

(52) U.S. Cl. .................. 422/104; 435/4; 435/6; 435/286.1; 435/286.2; 435/288.3; 435/288.7; 436/501; 436/164; 436/165; 436/172; 422/68.1; 422/82.05; 422/82.07; 422/82.08; 422/82.09; 250/234; 250/559.29

(58) Field of Classification Search .............. 435/4, 435/6, 286.1, 286.2, 287.1, 288.3, 288.7; 436/501, 164, 165, 172; 422/68.1, 82.05, 422/82.07–82.09, 104; 250/234, 559.29
See application file for complete search history.

(56) References Cited

U.S. PATENT DOCUMENTS

| | | | |
|---|---|---|---|
| 5,091,652 A | 2/1992 | Mathies et al. | |
| 5,260,578 A | 11/1993 | Bliton et al. | |
| 5,296,700 A | 3/1994 | Kumagai | |
| 5,324,633 A | 6/1994 | Fodor et al. | |
| 5,585,639 A | 12/1996 | Dorsel et al. | |
| 5,592,289 A * | 1/1997 | Norris | 356/244 |
| 5,671,054 A * | 9/1997 | Iwasaki | 356/631 |
| 5,760,951 A | 6/1998 | Dixon et al. | |

(Continued)

OTHER PUBLICATIONS

Agilent G2565AA "Microarray Scnner System with SureScan Technology" UserM anuel, Agilent Technologies,M ay 2002.

*Primary Examiner*—Mark L Shibuya
*Assistant Examiner*—Jacqueline Diramio (57) ABSTRACT

Array scanning methods that focus on the far side and devices configured for use in the same are provided. In reading arrays according to the subject methods, an array is placed in a reading position of a scanning device so that the nominal focal plane of the scanning device is present within the array substrate at a predetermined fixed substrate thickness fraction distance from the far-side of the array, and the array is then read by the device. As such, the subject scanner devices of the present invention are configured to hold an array substrate in a reading position of the device in which the device's nominal focal plane is present within the array substrate. The subject methods and devices find use in a variety of different applications, including both genomic and proteomic applications.

13 Claims, 2 Drawing Sheets

U.S. PATENT DOCUMENTS

| | | | |
|---|---|---|---|
| 5,763,870 | A | 6/1998 | Sadler et al. |
| 6,078,390 | A | 6/2000 | Bengtsson |
| 6,084,716 | A * | 7/2000 | Sanada et al. ............... 359/629 |
| 6,084,991 | A | 7/2000 | Sampas |
| 6,222,664 | B1 | 4/2001 | Dorsel |
| 6,222,666 | B1 * | 4/2001 | Moulin ...................... 359/246 |
| 6,284,465 | B1 | 9/2001 | Wolber |
| 6,320,196 | B1 | 11/2001 | Dorsel et al. |
| 6,371,370 | B2 | 4/2002 | Sadler et al. |
| 6,406,849 | B1 | 6/2002 | Dorsel et al. |
| 6,816,253 | B1 * | 11/2004 | Blaesing-Bangert et al. ......................... 356/244 |
| 6,835,938 | B2 * | 12/2004 | Ghosh et al. ............. 250/458.1 |
| 7,125,523 | B2 * | 10/2006 | Sillman ...................... 422/104 |
| 2003/0161514 | A1 * | 8/2003 | Curry ........................ 382/128 |
| 2004/0077099 | A1 * | 4/2004 | Yershov et al. ............. 436/164 |
| 2005/0057676 | A1 * | 3/2005 | Weiner et al. ............... 348/331 |
| 2005/0153349 | A1 * | 7/2005 | Ghosh et al. .................. 435/6 |
| 2005/0222777 | A1 * | 10/2005 | Kaushikkar .................. 702/19 |

\* cited by examiner

BIOPOLYMERIC ARRAY SCANNING DEVICES THAT FOCUS ON THE FAR SIDE OF AN ARRAY AND METHODS FOR USING THE SAME

FIELD OF THE INVENTION

This invention relates to biopolymer array optical scanners.

BACKGROUND OF THE INVENTION

Array assays between surface bound binding agents or probes and target molecules in solution are used to detect the presence of particular biopolymers. The surface-bound probes may be oligonucleotides, peptides, polypeptides, proteins, antibodies or other molecules capable of binding with target molecules in solution. Such binding interactions are the basis for many of the methods and devices used in a variety of different fields, e.g., genomics (in sequencing by hybridization, SNP detection, differential gene expression analysis, identification of novel genes, gene mapping, finger printing, etc.) and proteomics.

One typical array assay method involves biopolymeric probes immobilized in an array on a substrate such as a glass substrate or the like. A solution containing analytes that bind with the attached probes is placed in contact with the array substrate, covered with another substrate such as a coverslip or the like to form an assay area and placed in an environmentally controlled chamber such as an incubator or the like. Usually, the targets in the solution bind to the complementary probes on the substrate to form a binding complex. The pattern of binding by target molecules to biopolymer probe features or spots on the substrate produces a pattern on the surface of the substrate and provides desired information about the sample. In most instances, the target molecules are labeled with a detectable tag such as a fluorescent tag or chemiluminescent tag. The resultant binding interaction or complexes of binding pairs are then detected and read or interrogated, for example by optical means, although other methods may also be used. For example, laser light may be used to excite fluorescent tags, generating a signal only in those spots on the biochip that have a target molecule and thus a fluorescent tag bound to a probe molecule. This pattern may then be digitally scanned for computer analysis.

As such, optical scanners play an important role in many array-based applications. Optical scanners act like a large field fluorescence microscope in which the fluorescent pattern caused by binding of labeled molecules on the array surface is scanned. In this way, a laser induced fluorescence scanner provides for analyzing large numbers of different target molecules of interest, e.g., genes/mutations/alleles, in a biological sample.

The scanning equipment typically used for the evaluation of arrays includes a scanning fluorimeter. A number of different types of such devices are commercially available from different sources, such as Perkin-Elmer, Agilent, or Axon Instruments, etc. Analysis of the data, (i.e., collection, reconstruction of image, comparison and interpretation of data) is performed with associated computer systems and commercially available software, such as Quantarray™ by Perkin-Elmer, Genepix Pro™ by Axon Instructions, Microarray Suite™ by Affymetrix, as well as Feature Extraction Software and Rosetta Resolver Gene Expression Data Analysis System, both available from Agilent.

In such devices, a laser light source generates a collimated beam. The collimated beam is focused on the array and sequentially illuminates small surface regions of known location on an array substrate. The resulting fluorescence signals from the surface regions are collected either confocally (employing the same lens used to focus the laser light onto the array) or off-axis (using a separate lens positioned to one side of the lens used to focus the laser onto the array). The collected signals are then transmitted through appropriate spectral filters, to an optical detector. A recording device, such as a computer memory, records the detected signals and builds up a raster scan file of intensities as a function of position, or time as it relates to the position. Such intensities, as a function of position, are typically referred to in the art as "pixels". Biopolymer arrays are often scanned and/or scan results are often represented at 5 or 10 micron pixel resolution.

Scanning devices are generally configured so that the scanning lens of the device focuses on the front or near side of an array during reading. Front or near side focusing is appropriate where the ligand displaying surface of an array is the front or near side during reading.

However, in certain applications it is desirable to focus the scanning lens on the far side of an array, where the ligand displaying surface of the array is on the back side of the array relative to the scanning lens and the detected light passes through the transparent substrate of the array to reach the scanning lens. Far side focusing is desirable in certain applications as it can provide for low detection limits.

While various approaches have been developed for using a conventional front or near side scanning configured device to scan in a far side manner, such approaches are not completely satisfactory, e.g., they can result in decreased image quality. As such, there continues to be a need to develop methodology and devices for scanning the far side of an array.

SUMMARY OF THE INVENTION

Array scanning methods that focus on the far side of an array substrate and devices configured for use in the same are provided. In reading arrays according to the subject methods, an array is placed in a reading position of a scanning device so that the nominal focal plane of the scanning device is present within the array substrate, and the array is then read by the device. As such, the subject scanner devices of the present invention are configured to hold an array substrate in a reading position of the device in which the device's nominal focal plane is present within the array substrate, e.g., at a fixed substrate thickness fractional distance. The subject methods and devices find use in a variety of different applications, including both genomic and proteomic applications.

DEFINITIONS

Unless defined otherwise, all technical and scientific terms used herein have the same meaning as commonly understood by one of ordinary skill in the art to which this invention belongs. Still, certain elements are defined below for the sake of clarity and ease of reference.

A "biopolymer" is a polymer of one or more types of repeating units. Biopolymers are typically found in biological systems and particularly include polysaccharides (such as carbohydrates), peptides (which term is used to include polypeptides and proteins) and polynucleotides as well as their analogs such as those compounds composed of or containing amino acid analogs or non-amino acid groups, or nucleotide analogs or non-nucleotide groups. Biopolymers include polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic-acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. Biopolymers include DNA (including cDNA), RNA, oligonucleotides, and PNA and other polynucleotides as described in U.S. Pat. No. 5,948,902 and references cited therein (all of which are also incorporated herein by reference), regardless of the source. An "oligonucleotide" generally refers to a nucleotide multimer/polymer) of about 10 to 100 nucleotides in length, while a "polynucleotide" includes a nucleotide multimer having any number of nucleotides. A "biomonomer" references a single unit, which can be linked with the same or other biomonomers to form a biopolymer (e.g., a single amino acid or nucleotide with two linking groups one or both of which may have removable protecting groups).

An "array," includes any two-dimensional or substantially two-dimensional (as well as a three-dimensional) arrangement of addressable regions bearing a particular chemical moiety or moieties (e.g., biopolymers such as polynucleotide sequences (nucleic acids), polypeptides (e.g., proteins), etc.) associated with that region. In the broadest sense, the preferred arrays are arrays of polymeric binding agents, where the polymeric binding agents may be any of: polypeptides, proteins, nucleic acids, polysaccharides, synthetic mimetics of such biopolymeric binding agents, etc. In many embodiments of interest, the arrays are arrays of nucleic acids, including oligonucleotides, polynucleotides; cDNAs, mRNAs, synthetic mimetics thereof, and the like. Where the arrays are arrays of nucleic acids; the nucleic acids may be covalently attached to the arrays at any point along the nucleic acid chain, but are generally attached at one of their termini (e.g., the 3' or 5' terminus). Sometimes, the arrays are arrays of polypeptides, e.g., proteins or fragments thereof.

Any given substrate may carry one, two, four or more or more arrays disposed on a front surface of the substrate. Depending upon the use, any or all of the arrays may be the same or different from one another and each may contain multiple spots or features. A typical array may contain more than ten, more than one hundred, more than one thousand more ten thousand features, or even more than one hundred thousand features, in an area of less than 20 cm$^2$ or even less than 10 cm$^2$. For example, features may have widths (that is, diameter, for a round spot) in the range from a 10 μm to 1.0 cm. In other embodiments each feature may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents but may not be present when, for example, photolithographic array fabrication processes are used. It will be appreciated though, that the interfeature areas, when present, could be of various sizes and configurations Each array may cover an area of less than 100 cm$^2$ or even less than 50 cm$^2$, 10 cm$^2$ or 1 cm$^2$. In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulse jets of either polynucleotide precursor units (such as monomers) in the case of in situ fabrication, or the previously obtained polynucleotide. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used such as described in U.S. Pat. No. 5,599,695, U.S. Pat. No. 5,753,788, and U.S. Pat. No. 6,329,143. Interfeature areas need not be present particularly when the arrays are made by photolithographic methods as described in those patents.

An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probe" may be the one which is to be evaluated by the other (thus, either one could be an unknown mixture of polynucleotides to be evaluated by binding with the other). A "scan region" refers to a contiguous (preferably, rectangular) area in which the array spots or features of interest, as defined above, are found. The scan region is that portion of the total area illuminated from which the resulting fluorescence is detected and recorded. For the purposes of this invention, the scan region includes the entire area of the slide scanned in each pass of the lens, between the first feature of interest, and the last feature of interest, even if there exist intervening areas which lack features of interest. An "array layout" refers to one or more characteristics of the features, such as feature positioning on the substrate, one or more feature dimensions, and an indication of a moiety at a given location. "Hybridizing" and "binding", with respect to polynucleotides, are used interchangeably.

By "remote location," it is meant a location other than the location at which the array is present and hybridization occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top," "upper," and "lower" are used in a relative sense only.

A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means (see for instance, element 186 of FIG. 3) may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination which will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

DETAILED DESCRIPTION OF THE INVENTION array scanning methods that focus on the far side and devices configured for use in the same are provided. In reading arrays according to the subject methods, an array is placed in a reading position of a scanning device so that the nominal focal plane of the scanning device is present within the array substrate, typically at a predetermined fixed substrate thickness fractional distance from the far side of the array, and the array is then read by the device. As such, the subject scanner devices of the present invention are configured to hold an array substrate in a reading position of the device in which the device's nominal focal plane is present within the array substrate, e.g., at a fixed substrate thickness fractional distance from the far side of the array substrate. The subject methods and devices find use in a variety of different applications, including both genomic and proteomic applications.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In further describing the invention in greater detail than provided in the Summary and as informed by the Background and Definitions provided above, representative embodiments of the subject methods are described first in greater detail, followed by a review of representative scanning device embodiments of the of the invention. Also provided are discussions of representative applications in which the subject methods and devices find use.

Methods

As summarized above, the present invention provides a method for scanning or reading the far side of an array substrate when present in a reading position of a ligand (i.e., chemical, such as biopolymeric) array optical scanning or reading device. By "far side" is meant the array substrate surface that is distal from the scan lens of the reading device when the array substrate is in the reading position, such that emitted light from the far side substrate surface must pass through the substrate to reach the scan lens. As such, the far side is the side of the array substrate that is opposite or opposing the near side, where the near side of the substrate is the surface that is proximal to the scan lens and is the surface from which emitted light does not pass through the array substrate in order to reach the scan lens.

Specifically, the subject methods are methods of focusing the scan lens on the back or far side of an array substrate during reading, such that the scan lens is focused on the far side of the array substrate when the array substrate is present in the reading position. As such, in the subject methods, the array surface having the immobilized ligands of the array, i.e., the ligand displaying surface of the array, is the surface that is the far side of the array when the array is present in the reading position of the device.

In practicing the subject methods, the first step is to position the array to be read in the reading or scanning position of the device. A feature of the subject methods is that the array substrate is positioned in the reading position of the device such that the nominal focal plane of the device is present within the array substrate. By nominal focal plane is meant the focal plane positioned at the intersection of the paraxial rays of the scan lens in the absence of any substrate in the reading position of the device. More specifically, the nominal focal plane is a focal plane that is parallel to the front and back surfaces of a substrate when present in the reading position, where the intersection of the paraxial rays of the scan lens in the absence of an array substrate in the reading position is present in the nominal focal plane.

As the array substrate is positioned in the reading position of the device such that the nominal focal plane is located within the array substrate, the nominal focal plane is present between the front (or near) arid back (or far) surfaces or sides of the substrate when the array substrate is positioned in the reading or scanning position. Accordingly, the nominal focal plane divides or passes through the substrate parallel to the front and back surfaces when the substrate is positioned in the scanning position of the device.

In practicing the subject methods, the nominal focal plane is positioned within the substrate at a predetermined fixed substrate thickness fractional distance from the far side (i.e., ligand displaying surface) of the substrate. By predetermined fixed substrate thickness fractional distance is meant a known or preset distance from the far side of the substrate, where the known or preset distance is some fraction or portion of the overall thickness of the substrate. For example, where the thickness of a substrate is X, the predetermined fixed substrate thickness fractional distance is Y×X, where Y is a ratio between 0 and 1 and is predetermined or chosen based in the nature of the array substrate, and more specifically the index of refraction of the array substrate.

In the above formula, thickness X typically ranges from about 0.01 to about 5.0 mm, usually from about 0.1 to about 2 mm and more usually from about 0.5 to about 1.3 mm.

As mentioned above, Y is a ratio between 0 and 1 that is chosen or determined based on the particular composition of the array substrate to be scanned, and more specifically the index of refraction of the substrate to be scanned. For a given type of substrate having an index of refraction n, Y is chosen so that the nominal focal plane is at a distance $d=t-t/n$ from the back side, where t is the thickness and n the refractive index of the slide. Y typically varies between about 0.1 and about 0.9, and is more usually between about 0.2 and about 0.8, and in certain embodiments of interest, e.g., where the array substrate is glass, Y is between about 0.3 and about 0.4, e.g., 0.33

In certain embodiments, the scanner device employed in the subject methods has holder mechanism to hold the array in the reading position where the holder mechanism holds the array according to a predetermined fixed ratio Y, such that Y in the above formula cannot be adjusted for the scanner. Such embodiments are suitable where the same type of array substrate is going to be scanned in the device and any given substrate to be scanned will only vary with respect to thickness and not with respect to index of refraction. In such embodiments, one need only place the array in the holder, where the holder is configured to hold the array in the proper position where the location of the nominal focal plane in the substrate is located at the predetermined fixed substrate thickness fractional distance from the far side of the array substrate.

In yet other embodiments, the device employed is one in which the adjuster or array positioning element allows for a variable ratio Y, such that one can input a particular ratio Y into the device and the device selects a predetermined substrate thickness fractional distance based on the input value for Y. In these embodiments, the positioning step of the subject methods may include a step of inputting a variable ratio Y into the device (where the input could be in the form of the ratio itself or an input that the device employs to determine the variable ratio, e.g., from a look up table, where the input in this latter embodiment could be the type of substrate composition or the index of refraction for the substrate, etc.), where input of Y then causes the adjuster or array holder to hold the array at a fixed substrate thickness fractional distance that is selected or chosen for a given type of substrate. Such embodiments are typically practiced where one uses a device that is configured to be used with substrates of a variety of different types of compositions that vary with respect to each other in terms of index of refraction.

In certain embodiments, the actual position, i.e., predetermined fixed substrate thickness fractional distance, at which the nominal focal plane of the device is located in the substrate may include a contribution to account for aberrations caused by the substrate, e.g., spherical aberration of a plane plate for systems with high numerical aperture, where a slightly non-linear relationship between the substrate thickness and nominal focal plane location is desired. In such embodiments, the fixed substrate thickness fractional distance is one that takes into account a contribution to account for the above described desirable non-linear relationship, where the contribution may be determined empirically or theoretically, e.g., via ray tracing analysis. In such cases, the amount of adjustment to an initially determined fixed fractional distance (based solely on the type of substrate) typically ranges in magnitude from about +1 mm to about −1 mm, usually from about +0.1 mm to about −0.1 mm and more usually from about +0.1 mm to about −0.01 mm.

In the subject methods, once the array substrate is placed in the reading position of the scanner as described above, the array substrate is then read by the scanner. Specifically, by placing the array substrate in the reading position of the scanner as described above, the scan lens of the scanner is focused on and reads the back side of the array substrate (which is the ligand displaying surface of the ray). In other words, the scanner lens focuses on the far side or surface of the array substrate during reading.

The above general methods of reading an array find use in a variety of different applications, where representative applications are described below in greater detail.

It should be noted that while the above described methods are reviewed in terms of the nominal focal plane of a device, the subject methods are generally applicable to applications where a nominal object plane is employed by imaging the image plane back into object space with paraxial rays. As is obvious to someone skilled in the art, such cases are equivalent to the above for the following reason: The scan lens can be thought of as two lenses—one collimating rays from the sample, the other one focusing them into the image plane. So, taking the latter as a given, the above arguments apply equally for the nominal focal plane of the former.

Programming for practicing at least certain embodiments of the subject methods is also provided. For example, in certain embodiments as described above, the methods employ a device that provides for a variable ratio Y, which can be selected based on the nature of the particular substrate of the array to be scanned. In such methods, programming may be employed which allows a user to input a value from which the device may determine the appropriate predetermined fractional substrate thickness distance and then adjust the holder accordingly, i.e., adjust or modulate the array substrate positioner so that the array substrate, when positioned, is positioned in the correct place for scanning the far side of the substrate, as described above. The programming may be one that accepts a Y value directly, or one that selects the correct Y value based on input of a value from which Y can be determined (e.g., by referring to a look up table), where the value could be, e.g., the type of substrate composition, the index of refraction, etc.

Programming according to the present invention can be recorded on computer readable media, e.g., any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture that includes a recording of the present programming/algorithms for carrying out the above described methodology.

In certain embodiments, the system is further characterized in that it provides a user interface, where the user interface presents to a user the option of selecting among one or more different, including multiple different, Y inputs. Representative Y inputs for selection that the user interface could present include, but are not limited to: a Y value per se, the type of substrate to be scanned, the index of refraction of the substrate to be scanned, etc.

Optical Scanners

Also provided by the subject invention are biopolymer array optical scanners that are programmed as described above. A feature of the subject optical array scanners is that they include an array positioner or holder that holds an array substrate to be scanned in a reading position where the nominal focal plane of the device is present within the substrate. In other words, they include an array adjuster or holder that is configured to hold the array substrate when scanned by the reader in a position such that the scan lens focuses on the back side of the array, as described above.

In certain representative embodiments, the scanner holder or adjuster that positions the array in the reading position as described above is one that includes three pairs of reference points, where the three pairs of reference points or contacts move in a manner dependent on array substrate thickness. A feature of each of the pairs of the three pairs is that each pair of reference points is linked, such that the two reference points (i.e. substrate contacts) of a given pair are linked and cannot move independently relative to each other, at least when the array substrate is held in place by the positioner or holder.

The array positioner or holder, as described above, may be present in the scanner in a variety of different formats or configurations, including but not limited to: a lever mechanism, as described below; a stepper motor; adjustable screws; etc., where any convenient configuration may be present and the particular configuration chosen may depend, at least in part, on whether the scanner is one that is to be used with a single type of substrate, where the Y value may be fixed, or the scanner is one that is to be used with more than one type of substrate, where the Y value is adjustable or variable. In the former type of device, a lever type mechanism, such as the representative lever gear described below, may be present. In the latter type of device, an adjuster or holder mechanism that provides for more movement variability to account for the variable Y value may be present, such as one that includes a stepper motor or adjustable screws.

Figure 1:
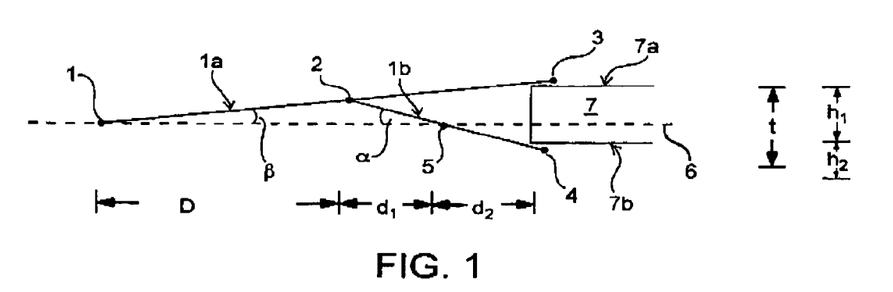
FIGS. 1 and 2 provide a schematic diagram of a two lever gear for holding an array substrate in a reading position of an array scanner according to the subject invention.

A representative gear mechanism for use in a device that is configured for a fixed ratio Y value of 0.33 (as is appropriate for glass substrates) is shown in FIG. 1. In FIG. 1, glass array substrate 7 has a near side 7a and far side 7b and is held by a pair of contact reference points (3 and 4), as described above, of a two lever gear made up of lever 1a and lever 1b. Lever 1b includes pivot 5 and contacts lever 1a at rotary joint 2. Lever 1a terminates at sliding point 1. In the two lever gear depicted in FIG. 1, d1 and d2 are equal to each other and ½ D, which provides for h2 being ⅓ of substrate thickness t and h1 being ⅔ of substrate thickness t. As such, the gear shown in FIG. 1 will hold glass substrates of various thickness within a certain range, e.g., from about 0.8 mm to about 1.3 mm in thickness, such that the nominal focal plane 6 is positioned ⅓ of thickness t from the far or back side 7b of the substrate 7.

Figure 2:
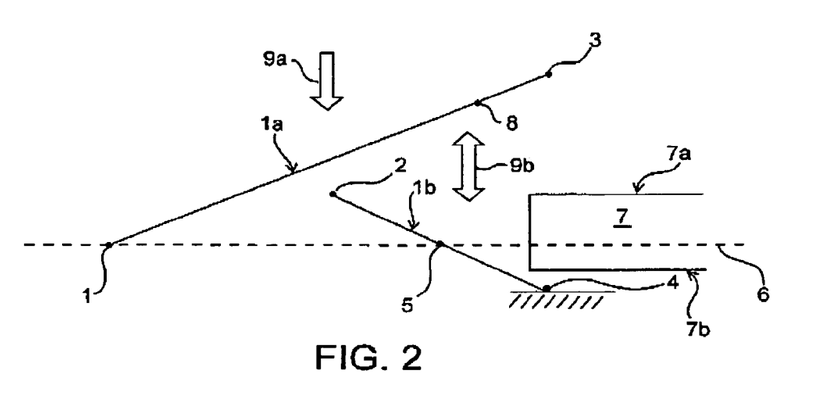

In the two lever gear depicted in FIG. 1, contact points 3 and 4 can be spring loaded against the glass substrate surface. To aid in loading the substrate into the holder, rotary joint 2 could be a roller as indicated in FIG. 2 that disengages as shown to allow ready placement of the substrate between the two levers. Rotary joint 2 could be configured to disengage when lever 1a is moved laterally by moving sliding point 1a sufficient distance in the direction of the substrate 7. In this embodiment, lever 1a is spring loaded in the direction of arrow 9a. Lateral movement of lever 1a in this embodiment can be limited by restricting movement of points 8, 3 and/or 4 to be in the vertical direction as shown by arrow 9b. When loading the array substrate in this embodiment, the array substrate is first placed between the contact points 3 and 4 and then point 1 is moved laterally in the direction away from the substrate such that contact points three and four contact the near and far side (7a and 7b, respectively) of the substrate and rotary joint 2 engages lever 1a. Again, because of the configuration of the lever, it automatically positions the substrate so that the nominal focal plane 6 is ⅓ t from the far side of the substrate.

In those embodiments where one desires a small non-linear correction on top of the linear function of the positioning of the nominal focal plane as a function of thickness, the lever could be modified to provide for this desired non-linear function, e.g., by having a curved contact surface for roller 2 in FIG. 2 to roll on, by having rotary joint 2 have an angle dependent profile, etc.

Figure 3:
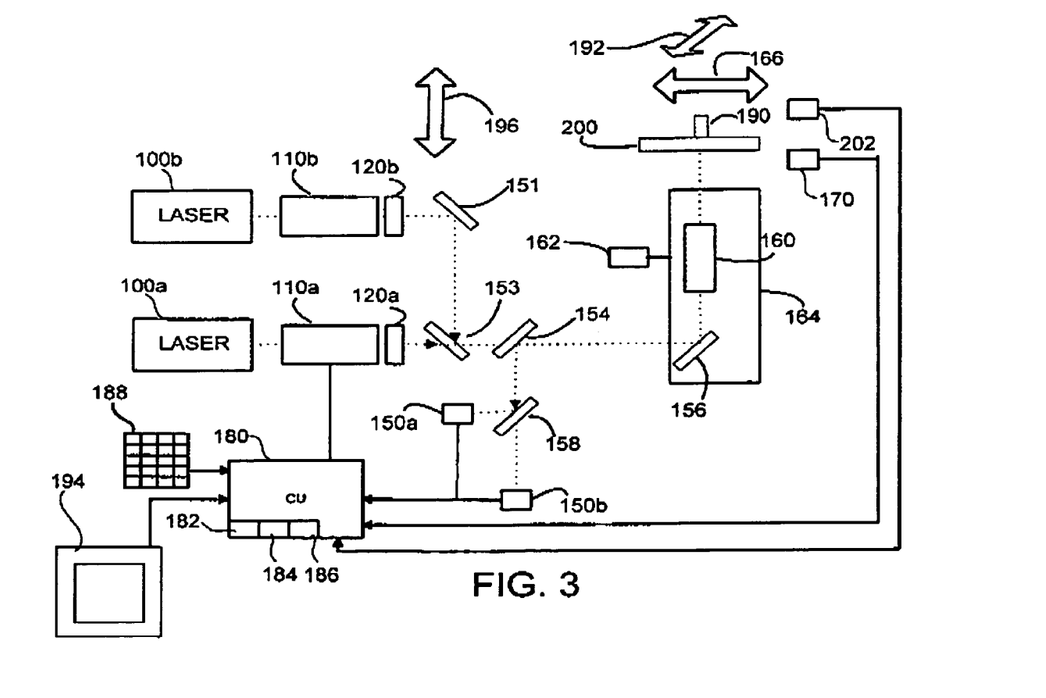
FIG. 3 schematically illustrates an optical scanner as may be used in the present invention.

Any biopolymer optical scanner or device may be provided to include the above array adjuster or holder (and optionally programming) as described above. Representative optical scanners of interest include those described in U.S. Pat. Nos: 5,585,639; 5,760,951; 5,763,870; 6,084,991; 6,222,664; 6,284,465; 6,320,196; 6,371,370 and 6,406,849—the disclosures of which are herein incorporated by reference. An exemplary optical scanner as may be used in the present invention is shown in FIG. 3.

A light system provides sample excitation light from an excitation light source, including a white light source, a laser, etc., where in many embodiments the excitation source is a laser, represented in the depicted system as element 100.

At least with respect to light produced by a laser, it passes through an electro-optic modulator (EOM) 110 with attached polarizer 120. Each laser 100a, 100b may be of different wavelength (e.g., one providing red light and the other green) and each has its own corresponding EOM 110a, 110b and polarizer 120a, 120b. The beams may be combined along a path toward a holder or caddy 200 (also referred to as positioner above) by the use of fold mirror 151 and dichroic mirror 153. A control signal in the form of a variable voltage applied to each corresponding EOM 110a, 110b by the controller (CU) 180, changes the polarization of the exiting light which is thus more or less attenuated by the corresponding polarizer 120a, 120b. Controller 180 may be or include a suitably programmed processor. Thus, each EOM 110 and corresponding polarizer 120 together act as a variable optical attenuator which can alter the power of an interrogating light spot exiting from the attenuator.

The remainder of the light from both lasers 100a, 100b is transmitted through a dichroic beam splitter 154, reflected off fully reflecting mirror 156 and focused onto either an array (not shown) mounted on holder 200, or a calibration member (not shown), whichever is at a reading position (chosen according to the method described above), using optical components in beam focuser 160. Light emitted (in particular, fluorescence) at two different wavelengths (e.g., green and red light) from features 16 (see FIG. 4) present on the far side of the array substrate relative to focuser/scanner 160, in response to the interrogating light, is imaged using the same optics in focuser/scanner 160, and is reflected off mirrors 156 and 154. The distinct excitation sources are aligned such that the emitted fluorescence passes through a further dichroic mirror 158 and are passed to respective detectors 150a and 150b.

More optical components (not shown) may be used between the dichroic mirror and each detector 150a, 150b (such as lenses, pinholes, filters, fibers, etca) and each detector 150a, 150b may be of various different types (e.g., a photo-multiplier tube (PMT) or a CCD or an avalanche photodiode (APD)). All of the optical components through, which light emitted from all array or calibration member in response to the illuminating laser light, passes to detectors 150a, 150b, together with those detectors, form a detection system. A scan system causes the illuminating region in the form of a light spot from each laser 100a, 100b, and a detecting region of each detector 150a, 150b (which detecting region will form a pixel in the detected image), to be scanned across multiple regions of an array or an array package mounted on holder 200.

The scanned regions for an array will include at least its multiple probe features. The scanning system is typically a line by line scanner, scanning the interrogating light in a line across an array as described below when at the reading position, in a direction of arrow(s) 166, then moving ("transitioning") the interrogating light in a direction into/out of the paper as depicted by arrow(s) 192 as viewed in FIG. 3 to a position at an end of a next line, and repeating the line scanning and transitioning until the entire array has been scanned.

This scanning feature is accomplished by providing a housing 164 containing mirror 156 and focuser 160, which housing 164 can be moved along a line of pixels (i.e., from left to right or the reverse as viewed In FIG. 3) by a transporter 162. The second direction 192 of scanning (line transitioning) can be provided by second transporter which may include a motor and belt (not shown) to move caddy 200 along one or more tracks. The second transporter may use a same or different actuator components to accomplish coarse (a larger number of lines) movement and finer movement (a smaller number of lines). Generally, directly adjacent rows are scanned. However, "adjacent" rows may include alternating rows or rows where more than one intervening row is skipped.

The scanner of FIG. 3 may further include a reader (not shown) to read an identifier from an array package. Such an identifier may be in the form of a bar that can be read by a suitable bar code reader.

Of course, the movements 166 and 192 may be accomplished by actuating holder 200 or housing 164 alone. Still further, the movement roles described for each element above may be swapped.

An autofocus detector 170 is generally provided to sense any offset (variation in slope) between different regions of array 12 when in the reading position, and a determined position of the focal plane of the detection system. The autofocus system includes detector 170, processor 180, and a motorized or servo-controlled adjuster 190 to move holder 200 in the direction of arrow 196 to establish correct focus for the system. The detector may directly detect a partial reflection from another beamsplitter (not shown) between splitters 153 and 154. In addition, a second position detector 202, also feeding back to the CU, preferably measures the absolute position (i.e., relative to the apparatus) of the servo-controlled adjuster 190). As above with respect to movements 166 and 192, it should be observed that focus servo control movement indicated by arrows(s) 196 may occur in connection with housing 164 instead of the holder. Further details regarding suitable chemical array autofocus hardware is described in pending U.S. patent application Ser. No. 09/415,184 for "Apparatus And Method For Autofocus" by Dorsel, et al., filed Oct. 7, 1999, the disclosure of which is herein incorporated by reference, as well as European publication EP 1091229 published Apr. 11, 2001 to the same title and inventors—the disclosure of the priority document of which is herein incorporated by reference. In addition, details regarding maintaining or setting lens focus upon changing direction may be appreciated in reference to U.S. patent application Ser. No. 10/087,220, entitled "Bi-Directional Scanner Control System," filed Feb. 28, 2002 which provides algorithms to account for variability in assay slide slope—the disclosure of which is herein incorporated by reference.

In any case, array orientation and configuration is of little consequence since focus is set to probe features looking through a transparent substrate medium, as described above, since the array is inverted for scanning.

Controller 180 of the apparatus is connected to receive signals from detectors 150*a*, 150*b*, these different signals corresponding to different "channels," i.e., signals which result at each of the multiple detected wavelengths from emitted light for each scanned region of an array when at the reading position mounted in holder 200. Controller 180 also receives the signal from autofocus offset detector 170 and absolute servo position detector 202, and provides the control signal to EOM 110, and controls the scan system. Controller 180 may also analyze, store, and/or output data relating to emitted signals received from detectors 150*a*, 150*b* in a known manner.

Controller 180 may include a computer in the form of a programmable digital processor, and include a media reader 182 which can read a portable removable media (such as a magnetic or optical disk), and a communication module 184 which can communicate over a communication channel (such as a network, for example the internet or a telephone network) with a remote site (such as a database at which information relating to array package 30 may be stored in association with the identification 40).

The controller is suitably programmed to execute all of the steps required by it during operation of the apparatus, as discussed further below. Alternatively, controller 180 may be any hardware or hardware/software combination which can execute those steps.

In certain embodiments, controller 180 includes programming as described above to adjust the holder in response to selection of a variable Y value, based on user input of Y or a parameter for selection of Y. To make selections, an input device 188 in the form of a keypad or keyboard may be provided. This may be a dedicated device or serve a number of input purposes. Alternately, input functions may be provided in connection with a touchscreen monitor 194 that could also be used to display data results and/or directions for use.

Utility

The subject biopolymer optical scanners find use in a variety of applications, where such applications are generally analyte detection applications in which the presence of a particular analyte in a given sample is detected at least qualitatively, if not quantitatively. Protocols for carrying out array assays are well known to those of skill in the art and need not be described in great detail here. Generally, the sample suspected of comprising the analyte of interest is contacted with an array under conditions sufficient for the analyte to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g., through use of a signal production system such as a fluorescent label present on the analyte, etc, where detection includes scanning with an optical scanner according to the present invention. The presence of the analyte in the sample is then deduced from the detection of binding complexes on the substrate surface.

Specific analyte detection applications of interest include hybridization assays in which the nucleic acid arrays of the subject invention are employed. In these assays, a sample of target nucleic acids is first prepared, where preparation may include labeling of the target nucleic acids with a label, e.g., a member of signal producing system. Following sample preparation, the sample is contacted with the array under hybridization conditions, whereby complexes are formed between target nucleic acids that are complementary to probe sequences attached to the array surface. The presence of hybridized complexes is then detected. Specific hybridization assays of interest which may be practiced using the subject arrays include: gene discovery assays, differential gene expression analysis assays; nucleic acid sequencing assays, and the like. References describing methods of using arrays in various applications include U.S. Pat. Nos. 5,143,854; 5,288, 644; 5,324,633; 5,432,049; 5,470,710; 5,492,806; 5,503,980; 5,510,270; 5,525,464; 5,547,839; 5,580,732; 5,661,028; 5,800,992—the disclosures of which are herein incorporated by reference.

Where the arrays are arrays of polypeptide binding agents, e.g., protein arrays, specific applications of interest include analyte detection/proteomics applications, including those described in U.S. Pat. Nos. 4,591,570; 5,171,695; 5,436,170; 5,486,452; 5,532,128 and 6,197,599 as well as published PCT application Nos. WO 99/39210; WO 00/04832; WO 00/04389; WO 00/04390; WO 00/54046; WO 00/63701; WO 01/14425 and WO 01/40803—the disclosures of which are herein incorporated by reference.

Figure 4:
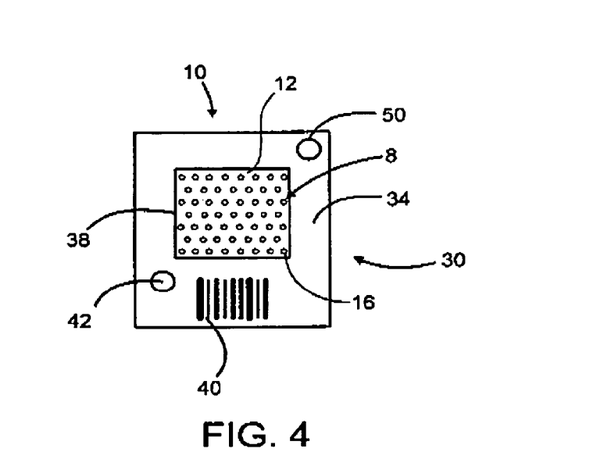
FIG. 4 is a front view of a packaged array that may be used in connection with the scanner of FIG. 3.

An example array is presented in FIG. 4. Array 10 carries multiple probe features 16 disposed across a surface of the substrate 12 upon which the array is formed. The substrate is preferably in the form of a contiguous, substantially planar substrate made of transparent material to facilitate data acquisition scanning there through. Alternatively, the substrate could be scanned from the side which carries features 16. Features 16 (not to scale) are shown disposed in a pattern which defines the array. The extent of the pattern defines a scan region 8.

Array 10 may be set within a housing 34 to provide an array package 30. In which case, substrate 12 is sealed (such as by the use of a suitable adhesive) to housing 34 around a margin 38. Housing 34 is configured such that housing 34 and substrate 12, define a chamber into which features 16 of the array face. This chamber is accessible through resilient septa 42, 50 which define normally closed ports of the chamber. An identifier 40, possibly in the form of a bar code, may be affixed to housing 34. The above description is merely exemplary of a package design that may be employed, where other package designs are known and may be used, including the package design sold by Agilent for use in its G2565AA Microarray Scanner System. The composition of the probe features and material(s) used to produce elements of the array package may vary, but may be as typical in the art.

In using an array in connection with a programmed scanner according to the present invention, the array will typically be exposed to a sample (such as a fluorescently labeled analyte, e.g., protein containing sample) and the array then read. Reading of the array may be accomplished by illuminating the array and reading the location and intensity of resulting fluorescence at each feature of the array to detect any binding complexes on the surface of the array.

It is further noted that aspects of the invention may be applicable to a variety of optical scanners including those that detect chemiluminescent or electroluminescent labels. The present invention will be applicable to such scanners where powering down the scanner will result in lifetime savings, as exemplified above.

In any case, results from reading an array may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample). The results of the reading (processed or not) may be forwarded (such as by communication) to a remote location if desired, and received there for further use (such as further processing). Stated otherwise, in certain variations, the subject methods may include a step of transmitting data from at least one of the detecting and deriving steps, to a remote location. The data may be transmitted to the remote location for further evaluation and/or use. Any convenient telecommunications means may be employed for transmitting the data, e.g., facsimile, modem, internet, etc.

Kits

Kits for use in connection with the subject invention may also be provided. Such kits preferably include at least a computer readable medium including programming as discussed above and instructions. The instructions may include installation or setup directions. The instructions may include directions for use of the invention with options or combinations of options as described above. In certain embodiments, the instructions include both types of information.

Providing the software and instructions as a kit may serve a number of purposes. The combination may be packaged and purchased as a means of upgrading an existing scanner. Alternately, the combination may be provided in connection with a new scanner in which the software is preloaded on the same. In which case, the instructions will serve as a reference manual (or a part thereof and the computer readable medium as a backup copy to the preloaded utility.

The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the kit, but means for obtaining the instructions from a remote source, e.g. via the Internet, are provided. An example of this embodiment is a kit that includes a web address where the instructions can be viewed and/or from which the instructions can be downloaded. Conversely, means may be provided for obtaining the subject programming from a remote source, such as by providing a web address. Still further, the kit may be one in which both the instructions and software are obtained or downloaded from a remote source, as in the Internet or world wide web. Some form of access security or identification protocol may be used to limit access to those entitled to use the subject invention. As with the instructions, the means for obtaining the instructions and/or programming is generally recorded on a suitable recording medium.

It is evident from the above discussion that the above described invention provides an effective and readily applicable way to scan the far side or back side of an array, which provides for a number of benefits include low limits of detection. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A ligand array scanner device for reading an array comprising a substrate having a surface displaying two or more ligands, said device comprising:
   an array holder for holding said array in a reading position, wherein said array holder comprises three pairs of reference points that move in a manner dependent on said substrate thickness wherein said array holder is adjustable, and
   a scan lens, wherein the holder is configured to hold said substrate between each pair of the three pairs of reference points, wherein for each pair of reference points, one reference point contacts the substrate surface distal from the scan lens and the other reference point contacts the substrate surface proximal to the scan lens.

2. The device according to claim 1, wherein each pair of said reference points comprises linked reference points.

3. The device according to claim 2, wherein said linked reference points cannot move independently relative to each other.

4. The device according to claim 1, wherein said array holder is configured to hold said array substrate so that said device's nominal focal plane is positioned at a predetermined substrate thickness fractional distance from said ligand displaying surface of said array substrate.

5. The device according to claim 4, wherein said predetermined substrate thickness fractional distance is a fixed ratio.

6. The device according to claim 4, wherein said predetermined substrate fractional distance is a variable ratio and said device modulates the manner in which said holder holds said array based in selection of said variable ratio.

7. The device according to claim 1, further comprising a computer-readable medium comprising programming that adjusts the position of said array holder based on a determination of a substrate thickness fractional distance selected based on a substrate index of refraction input.

8. The device according to claim 1, further comprising an electro-optic modulator (EOM) and a polarizer.

9. The device according to claim 1, further comprising said array held in said holder.

10. The device according to claim 9, wherein said array is an addressable polynucleotide array.

11. The device according to claim 9, wherein said array is an addressable polypeptide array.

12. The device according to claim 5, wherein said array holder comprises a lever mechanism.

13. The device according to claim 6, wherein said array holder comprises a stepper motor or adjustable screws.

* * * * *